US005081995A

United States Patent [19]

Lu et al.

[11] Patent Number: 5,081,995

[45] Date of Patent: Jan. 21, 1992

[54] ULTRASONIC NONDIFFRACTING TRANSDUCER

[75] Inventors: Jian-yu Lu; James F. Greenleaf, both of Rochester, Minn.

[73] Assignee: Mayo Foundation for Medical Education and Research, Rochester, Minn.

[21] Appl. No.: 471,457

[22] Filed: Jan. 29, 1990

[51] Int. Cl.[5] .................. A61B 8/00

[52] U.S. Cl. .................. 128/662.03; 310/369

[58] Field of Search .................. 128/660.01, 662.03, 128/; 73/625-626; 310/334, 358, 369

[56] References Cited

U.S. PATENT DOCUMENTS

| | | | |
|---|---|---|---|
| 2,875,355 | 2/1959 | Peterman | 73/625 |
| 4,117,446 | 9/1978 | Alais | 73/626 |
| 4,145,931 | 3/1979 | Tancrell | 73/626 |
| 4,586,512 | 5/1986 | Do-huu et al. | 128/661.01 |
| 4,677,981 | 7/1987 | Coursant | 128/660.07 |

OTHER PUBLICATIONS

"Exact Solutions for Nondiffracting Beams, I, The Scalar Theory", by J. Durnin, vol. 4, No. 4/Apr. 1987/J. Opt. Soc. Am. A., pp. 651-654.

"Diffraction-Free Beams", by J. Durnin et al, 1986 Annual Meeting, Optical Society of America, p. 128.

"Diffraction-Free Beams", by J. Durnin et al, Physical Review Letters, vol. 58, Apr. 13, '87, No. 15, pp. 1499-1501.

"Bessel-Gauss Beams", by F. Gori et al, Optics Comm., vol. 64, No. 6, Dec. 15, '87, pp. 491-495.

"Modal Expansion for $J_o$-Correlated Schell-Model Sources", by F. Gori et al, Optics Comm., vol. 64, No. 4, Nov. 15, '87, pp. 311-316.

"Introduction to Fourier Optics", by Joseph W. Goodman, McGraw-Hill Book Company.

"Directionality of Partially Coherent Bessel-Gauss Beams", by M. Zahid et al, Optics Comm., vol. 70, No. 5, Apr. 1, '89, pp. 361-364.

"Bessel Beam Ultrasonic Transducer: Fabrication Method and Experimental Results", by D. K. Hsu et al, Applied Physics Letters, Nov. '89.

"Evidence of Localized Wave Transmission", by Richard W. Ziolkowski et al, Physical Review Letters, vol. 62, No. 2, Jan. 9, '89.

"The Role of Piezocomposites in Ultrasonic Transducers", by Wallace Arden Smith, 1989 IEEE Ultrasonics Symposium.

"Ultrasonic Transducer with a Two-Dimensional Gaussian Field Profile", by Richard O. Claus et al, IEEE Transactions on Sonics and Ultrasonics, vol. 30, No. 1, Jan. '83.

*Primary Examiner*—Francis Jaworski
*Attorney, Agent, or Firm*—Quarles & Brady

[57] ABSTRACT

An ultrasonic transducer for use in medical imaging systems includes a piezoelectric element having an active electrode formed as a series of concentric annular segments. Each segment is separately driven by a transmitter in which the amplitude and phase of the drive signals produce an ultrasonic wave having a pressure profile that approxinmates a zeroth order Bessel function. A nondiffracting beam of ultrasonic waves is produced.

7 Claims, 4 Drawing Sheets

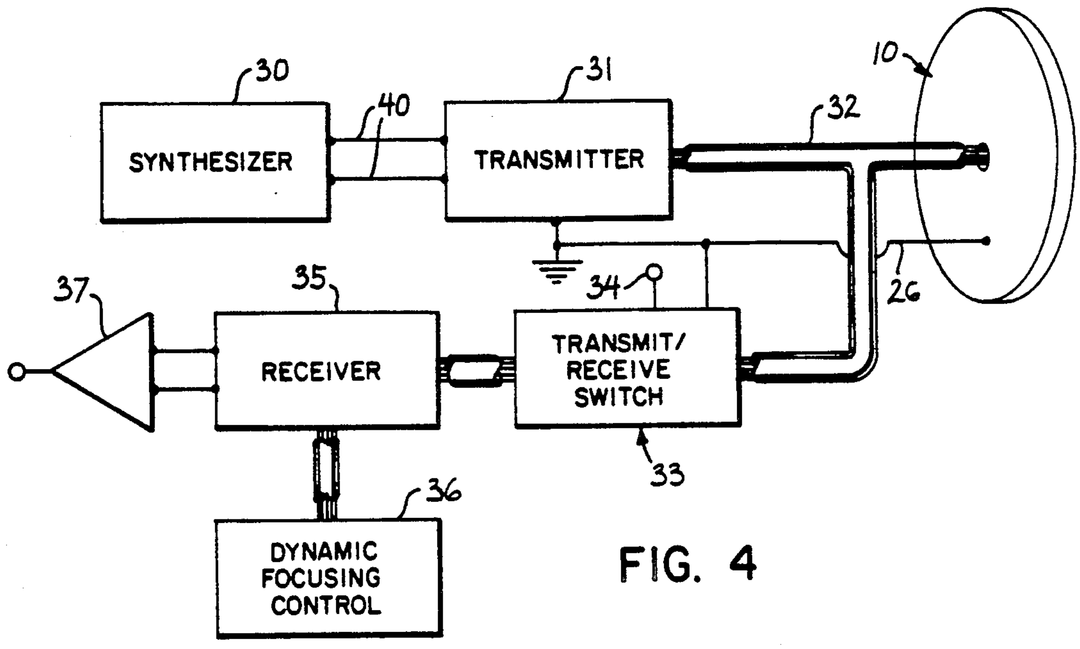
FIG. 4
FIG. 5
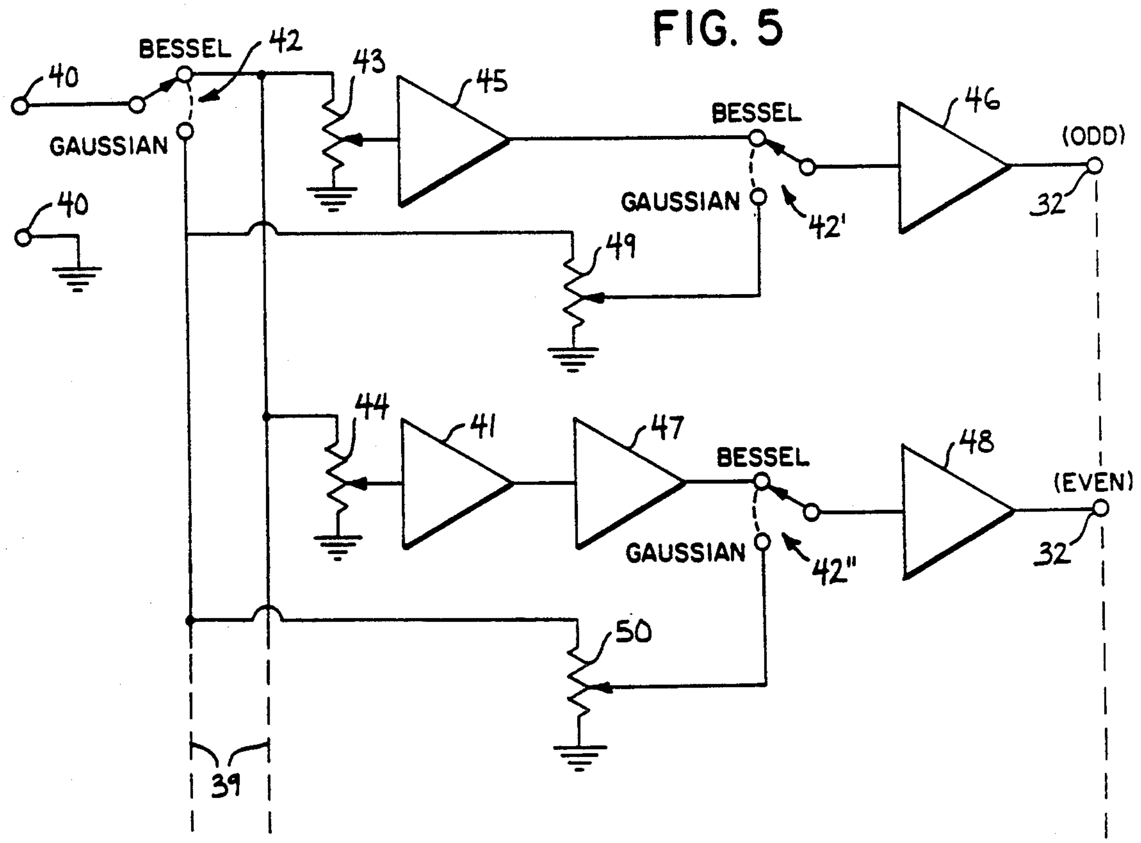

ULTRASONIC NONDIFFRACTING TRANSDUCER

BACKGROUND OF THE INVENTION

The field of the invention is ultrasonic transducers which radiate ultrasonic waves into the body of a patient and which receive and detect ultrasonic waves emanating from the body of a patient.

Ultrasonic transducers for medical applications are constructed from one or more piezoelectric elements which are sandwiched between a pair of electrodes. Such piezoelectric elements are typically constructed of lead zirconate titanate (PZT), polyvinylidene diflouride (PVDF), or PZT ceramic/polymer composite. The electrodes are connected to a voltage source, and when a voltage is applied, the piezoelectric elements change in size at a frequency corresponding to that of the applied voltage. When a voltage pulse having an ultrasonic frequency is applied, the piezoelectric element emits an ultrasonic wave in the media to which it is coupled. Conversely, when an ultrasonic wave strikes the piezoelectric element, the element produces a corresponding voltage across its electrodes. Typically, the front of the element is covered with an acoustic matching layer that improves the coupling with the media in which the ultrasonic waves propagate. In addition, a backing material is disposed to the rear of the piezoelectric element to absorb ultrasonic waves that emerge from the back side of the element so that they do not interfere.

When used for ultrasound tomography, the transducer has a number of piezoelectric elements arranged in an array and driven with separate voltages (apodizing). By controlling the phase of the applied voltages, the ultrasonic waves produced by the piezoelectric elements combine to produce a net ultrasonic wave which is focused at a selected point. By controlling the phase of the applied voltages, this focal point can be moved in an azimuthal plane to scan the subject. However, objects which are not at the focal plane which is orthogonal to the azimuthal plane and parallel to the surface of the array are out of focus and their resolution in the reconstructed image is reduced. Thus, ultrasonic transducers focus the wave providing very high resolution images of objects lying at or near the focal plane, but have increasingly lower resolution of objects lying to either side of this plane. Such transducers are said to have high resolution, but low depth of field.

In very high quality medical imaging equipment ultrasonic transducers having an array of annular shaped piezoelectric elements have been used. Such prior transducers are driven by Gaussian shaded or Fresnel shaped voltages to provide high resolution within a relatively shallow depth of field. Outside the depth of field the resolution degrades due to diffraction effects.

Nondiffracting solutions to the wave equation governing their propagation (the scalar Helmholtz equation) have recently been discovered and extensively tested with electromagnetic waves. This solution was described by J. Durnin in an article "Exact Solutions for Nondiffracting Beams. I. The Scalar Theory." published in the *Journal of Optical Society of America* 4(4):651-654, in April, 1987. This solution indicates that transducers can be constructed which produce a wave that is confined to a beam that does not diffract, or spread, over a long distance. Such a nondiffractive beam can produce a much greater depth of field than a focused Gaussian beam.

SUMMARY OF THE INVENTION

The present invention relates to an ultrasonic transducer for medical imaging systems in which the elements of the transducer are shaped to produce a nondiffracting ultrasonic beam when driven by voltages of the proper phase and amplitude. More specifically, the present invention is an ultrasonic transducer system having a piezoelectric element, a grounding electrode attached to one side of the piezoelectric element, a set of active electrodes attached to the other side of the piezoelectric element which have dimensions determined by a Bessel function nondiffracting solution to the scalar wave equation, and a multi-channel transmitter which drives each active successive electrode with a separate voltage and with alternate phases. The resulting Bessel shaded ultrasonic transducer produces a beam of ultrasonic energy which does not diffract over a selected distance.

A general object of the invention is to provide an ultrasonic transducer for medical imaging systems which provides improved depth of field. The Bessel shaded transducer system produces a nondiffracting beam over a large distance, or depth, and this results in relatively high and constant resolution of objects throughout this depth.

Another object of the invention is to provide a nondiffracting ultrasonic transducer system which is easily and economically manufactured. One nondiffracting solution to the wave equation can be approximated by a disc shaped grounding electrode disposed on a flat surface of the piezoelectric element, and a set of annular shaped active electrodes disposed on a flat opposite surface of the piezoelectric element. The multi-channel voltage source applies the ultrasonic voltage to the respective annular shaped active electrodes with alternating polarity. Manufacturing methods used to make conventional piezoelectric transducers can thus be used to make the nondiffracting transducer of the present invention without the need for special machining and poling.

Another object of the invention is to provide an ultrasonic transducer for medical imaging systems in which either a nondiffracting beam or a Gaussian beam may be transmitted or received. The multi-channel transmitter and receiver contains separate shading potentiometers and inverters which can be switched between a Bessel shaded nondiffracting mode and a Gaussian shaded mode. The transmitter can be switched to the BESSEL mode to launch a non-diffracting beam of ultrasound into the patient, for example, and the receiver can be switched to the GAUSSIAN mode to receive reflections from the focal point which will be changed as the wave travels towards the transducer.

Another object of the invention is to provide an ultrasonic transducer for tissue characterization. The multi-channel transmitter and receiver can produce a nondiffracting beam and can receive the signals scattered from tissues without diffraction, which makes the correction for diffraction negligible in the estimation of parameters of tissues. For example, one can determine the ultrasonic attenuation of biological tissue by adjusting the gain compensation to make the backscattered signals from the tissue to be of equal brightness, the setting of the gain along the distance will give the reading of attenuation if there is no diffraction.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 4 is a block diagram of the ultrasonic transmitter and receiver system which employs the transducer of FIG. 1;

FIG. 5 is an electrical schematic diagram of a transmitter which is employed in the system of FIG. 4;

DESCRIPTION OF THE PREFERRED EMBODIMENT

Figure 2:
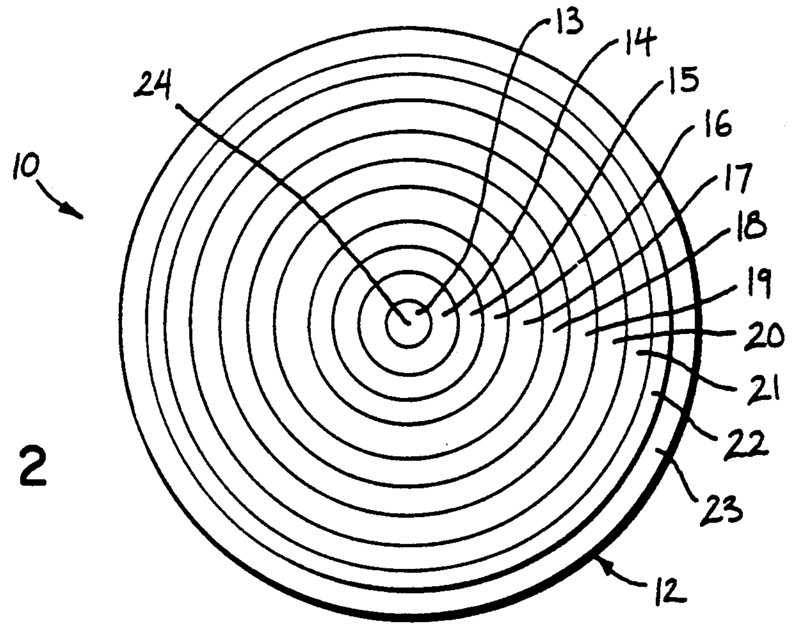
FIG. 2 is a plan view of the active electrodes which form one layer in the transducer of FIG. 1.

Nondiffracting solutions to the wave equation governing the propagation of electromagnetic waves have been proposed and tested. The present invention is an ultrasonic transducer and its associated circuitry which employs a nondiffracting solution to the wave equation to improve the performance of the transducer in medical applications.

The source-free scalar wave equation is given by:

$$\left(\nabla^2 - \frac{1}{C^2}\frac{\partial^2}{\partial t^2}\right)U(\vec{r},t) = 0. \qquad (1)$$

A nondiffracting solution to this scalar wave equation is:

$$U(\vec{r},t) = e^{i(\beta z - wt)}\left[\int_0^{2\pi} A(\phi)\, e^{-i\alpha(x\cos\phi + y\sin\phi)}d\phi\right], \qquad (2)$$

where $$\begin{cases} \alpha^2 + \beta^2 = k^2, \left(k = \frac{w}{c}\right); \\ 0 < \alpha \leqq k \end{cases} \qquad (3)$$

$A(\phi)$ is an arbitrary complex function of $\phi$, $\beta$ is real, $\vec{r}$ represents the observing point, t is time, w is angular frequency of the sound, and c is the speed of sound, If A ($\phi$) is independent of $\phi$, one obtains the simplest, axially symmetric, nondiffracting solution, which is proportional to $$U(\vec{r},t) = J_o(\alpha\rho)e^{i(\beta z - wt)}, \qquad (4)$$

where $J_o$ is the zeroth order Bessel function of the first kind. From Equation 4, it is seen that the beam pattern of the $J_o$ Bessel nondiffracting solution is independent of distance, z. This means that the $J_o$ Bessel beam will travel to infinity without spreading.

In practical applications, a transducer of finite aperture is used and in this case, a formula that determines the maximum nondiffracting distance of the $J_o$ Bessel beam is as follows:

$$z_{max} = a\sqrt{(k/\alpha)^2 - 1}). \qquad (5)$$

Figure 7:
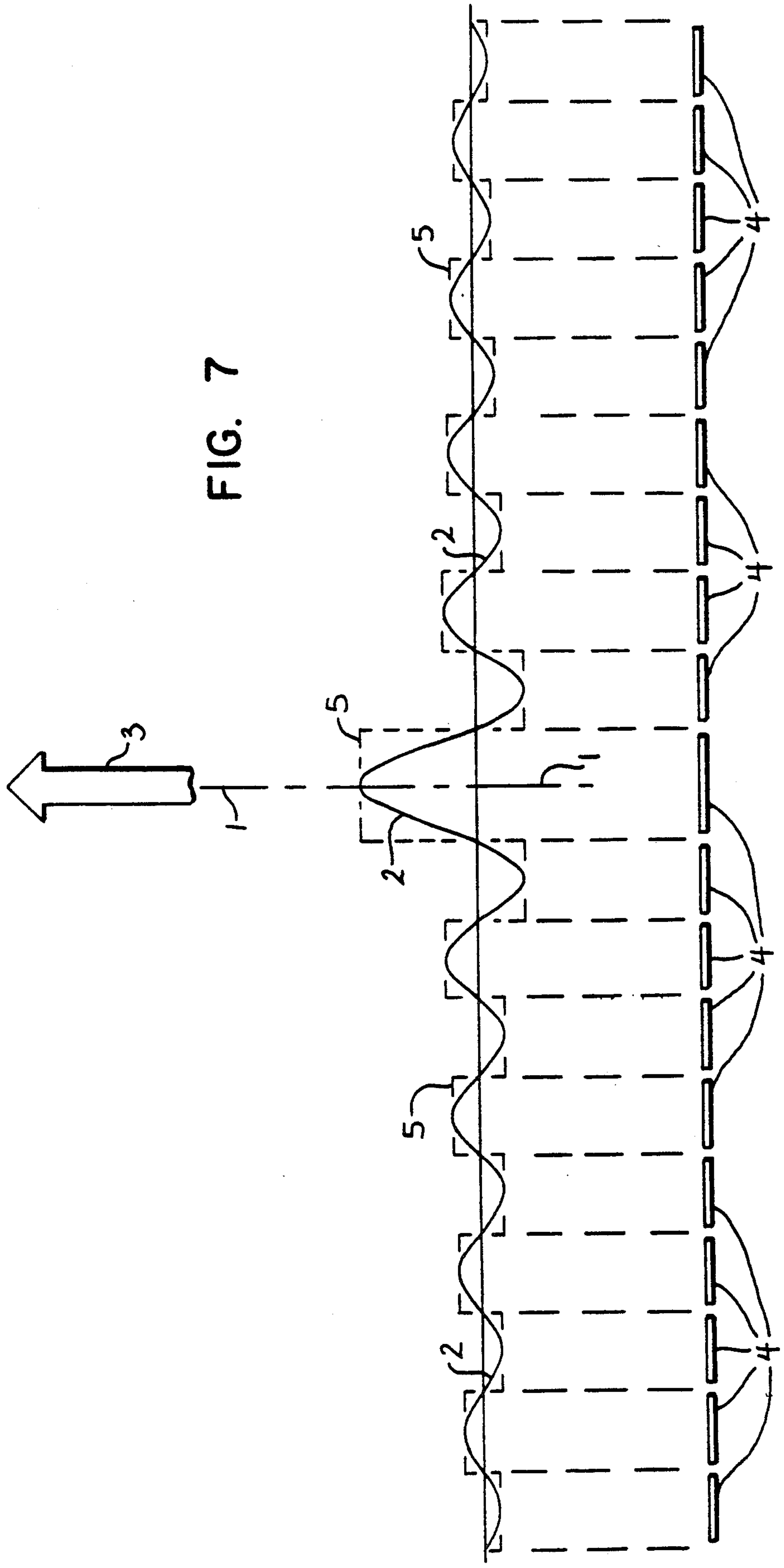
FIG. 7 is a graphic representation of the profile of a zeroth order Bessel function and the ultrasound pressure profile produced by an ultrasonic transducer according to the present invention.

Referring to FIG. 7, a zeroth order Bessel function $J_o$ is plotted as a function of distance from a central axis 1 and is represented by solid line 2. The above solution to the wave equation indicates that if the surface of a transducer is shaped to undulate as illustrated by line 2 and is uniformly excited to launch a wave, that a beam of pressure indicated by the arrow 3 will be produced along the central axis 1 and will not diffract, or spread, over a large depth of field. The difficulty, of course, is how to economically manufacture such a transducer.

The solution presented by the present invention is to approximate the Bessel function pressure distribution profile represented by line 2 using an ultrasonic transducer which is easily manufactured using current methods. More specifically, an ultrasonic transducer is constructed which has a set of electrode segments 4 that are disposed on a substantially flat surface and are dimensioned to correspond in relative size and relative position to the lobes on the zeroth order Bessel function. Since the electrode segments are driven with separate voltages, a small insulating gap is required between them. Conventional manufacturing methods can be used to construct this transducer.

Each segment 4 of the electrode is separately driven with a signal that has a relative amplitude and polarity which corresponds to its associated lobe in the zeroth order Bessel function. This is illustrated in FIG. 7 by the dashed line 5 which alternates in polarity for each lobe/segment and which has a relative amplitude equal to the relative peak values of each successive lobe. In other words, a non-diffracting Bessel function beam is produced from the flat electrode segments 4 by properly dimensioning them as described above and illustrated in FIG. 7, and by applying separate signals to them which alternate in polarity and which have relative amplitudes that correspond to the Bessel function lobe peak values.

Figure 1:
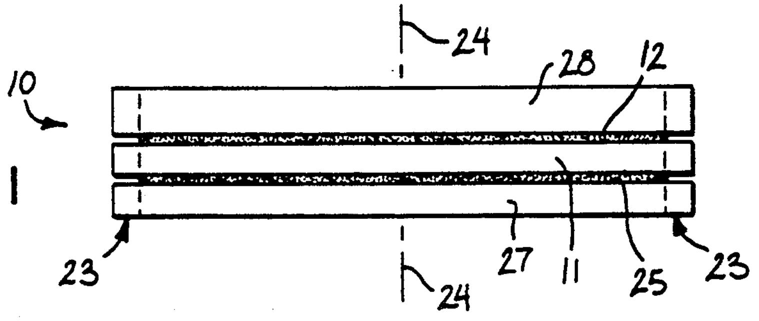
FIG. 1 is a view in cross section through a preferred embodiment of an ultrasonic transducer made according to the present invention.
Figure 3:
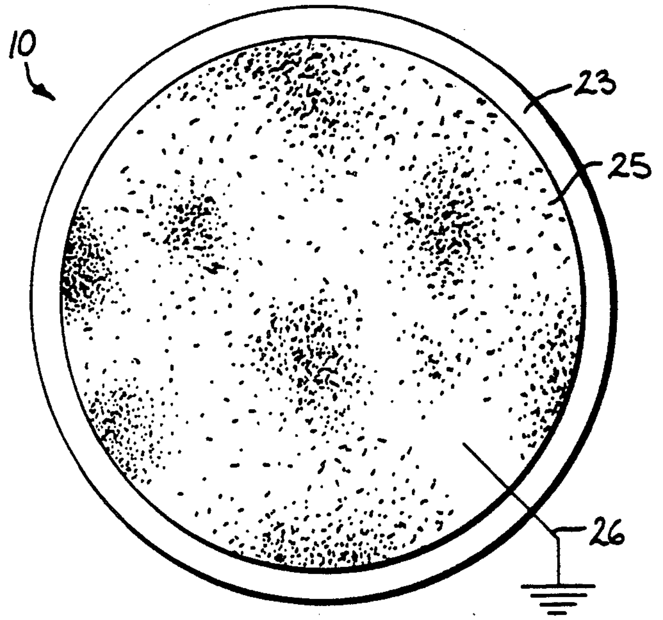
FIG. 3 is a plan view of the ground electrode which forms another layer in the transducer of FIG. 1.

An ultrasonic transducer 10 which will produce a field according to the above equations is shown in FIGS. 1–3. The transducer 10 includes a piezoelectric element 11 formed from a piezoelectric material such as lead zirconate titanate which is well-known in the art as "PZT." The piezoelectric element 11 has a thickness which is determined by the speed of sound in the piezoelectric element and the desired center frequency of 2.5 MHz. In the preferred embodiment the element 11 has a thickness of 0.6 mm and a diameter of 50 mm. Disposed on the back surface of the piezoelectric element 11 is an active electrode 12 in the form of a conductive metal layer which is shaped to form a central segment 13 and nine annular shaped segments 14–22. An inactive ring 23 surrounds the active electrode 12 and is used for mounting purposes. The dimensions of the active electrode segments 13–22 are calculated based on the above equations to produce the following sizes:

| Segment No. | Inside radius | Outside Radius |
|---|---|---|
| 13 | | 1.90 mm |
| 14 | 2.10 mm | 4.49 mm |
| 15 | 4.69 mm | 7.10 mm |
| 16 | 7.30 mm | 9.71 mm |
| 17 | 9.91 mm | 12.30 mm |
| 18 | 12.50 mm | 14.90 mm |
| 19 | 15.10 mm | 17.50 mm |
| 20 | 17.70 mm | 20.20 mm |
| 21 | 20.40 mm | 22.80 mm |
| 22 | 23.00 mm | 25.00 mm |

The active electrode segments are separated from one another by approximately .2 mm and electrically insulated from each other. They are coaxial with a central axis 24 that extends perpendicular from the central segment 13. A lead wire (not shown in FIGS. 1–3) connects to each active electrode segment 13–22 so that each can be driven by a separate voltage, or the signal produced at each active electrode element can be separately received as described below.

Referring still to FIGS. 1–3, a ground electrode 25 is disposed on the front surface of the piezoelectric element 11. The ground electrode 25 is a conductive metal layer of circular shape which has a radius of 25 mm and which is coaxial with the active electrode segments 13–22. A single lead 26 connects the ground electrode 25 to the circuit ground of the transmitter and receiver circuits. The inactive ring 23 surrounds the ground electrode 25.

Formed on the front of the piezoelectric element 11 and over the entire surface of the ground electrode 25 is an impedance matching layer 27. The layer 27 is made from a polymer, and as is well-known in the art, its purpose is to match the acoustic impedance of the piezoelectric element 11 to the impedance of the media into which the acoustic waves are to be propagated. In medical applications that media is tissue. Disposed on the back surface of the piezoelectric element 11, and covering the entire surface of the active electrodes 12, is an ultrasonic wave absorber 28. The wave absorber is made from a material containing wideband scatterers and its purpose is to absorb the ultrasonic wave emanating from the back surface of the piezoelectric element 11 so that it does not interfere with the wave propagated from and received at the front surface of the piezoelectric element 11.

As is well-known in the art, when a voltage is applied across the active electrode and ground electrode the piezoelectric element 11 changes thickness. By varying the voltage at a ultrasonic frequency the corresponding changes in thickness generate an ultrasonic wave which is conveyed into the patient by the impedance matching layer 27. The frequency, phase, and amplitude of the applied voltage determines the frequency, phase and amplitude of the resulting ultrasonic wave. Conversely, when an ultrasonic wave is received by the transducer 10, it physically effects the piezoelectric element 11 which produces corresponding voltages across its electrodes 12 and 25.

While the active electrode 12 is disposed on the back surface of the piezoelectric element 11 in the preferred embodiment, it is also possible to switch the positions of the active electrode 12 and ground electrode 25 without affecting the operation of the transducer 10. In medical applications it is preferable to have the ground electrode 25 closer to the patient and to further remove the active electrode 12 which has high voltage applied to it.

A system which employs the transducer 10 is illustrated in FIG. 4. The system includes a synthesizer 30 which produces either a 2.5 MHz continuous signal for CW operation, or controlled pulses of 2.5 MHz center frequency for pulse operation. The output of the synthesizer 30 is applied to a transmitter 31 which amplifies the 2.5 MHz signal and separately applies it through a cable 32 to each of the ten elements 13–22. The amplitude and polarity of the applied signals are separately controlled by the transmitter 31, as will be described in more detail below, such that the transducer 10 emits a non-diffractive beam of ultrasonic energy at a nominal center frequency of 2.5 MHz. It can be appreciated by those skilled in the art that the center frequency of the transducer can be changed to operate at other frequencies, which in medical applications range from 1.0 to 15.0 MHz.

Referring still to FIG. 4, the ten leads in the cable 32 also connect to a transmit/receive switch circuit 33 and when the transmitter 31 is turned off, the circuit 33 is operated through a control line 34 to switch signals received from the transducer 10 to a receiver 35. As will be described below, the receiver 35 has ten separate channels, one for each active segment 13–22 in the transducer 10, and each channel is separately controlled by a dynamic focusing control circuit 36. The ten separate signals are combined and applied to an output amplifier 37 which produces a single signal that is processed to produce the desired medical image in the well-known manner.

Referring particularly to FIG. 5, the transmitter 31 contains the separate channels which receive the input signal from the synthesizer 30 through leads 40. Only two channels of the transmitter 31 are shown in FIG. 5, one of them exemplifying all of the odd numbered channels (i.e. drive segments 13, 15, 17, 19 and 21) and the other exemplifying all of the even numbered channels (i.e. drive segments 14, 16, 18, 20 and 22). As will become apparent, the circuitry is the same for all ten channels, except the even channels have an additional inverter 41 which inverts, or shifts the phase of the signals applied to the even active elements 14, 16, 18, 20 and 22 by 180°. The connections for the eight additional channels are indicated by the dashed lines 39.

Referring particularly to FIG. 5, the input signal from the synthesizer 30 is coupled through a mode switch 42 to the inputs of the ten separate channels. When the mode switch is in the "BESSEL" mode, the signal is applied to respective shading potentiometers 43 and 44 at the input of each channel. In the odd numbered channels, the signal from the shading potentiometer 43 is applied to a low level buffer amplifier 45 which drives a high level buffer amplifier 46 through a second pole 42' on the mode switch. In the even numbered channels, the signal from the shading potentiometer 44 is applied through the inverter 41 to a low level buffer amplifier 47, which in turn drives a high level buffer amplifier through a third pole 42" on the mode switch. Consequently, when the mode switch is set to "BESSEL", the polarity of the signals applied to successive segments of the active electrode 12 (FIG. 2) alternate and the amplitude of successive signals are separately determined by shading potentiometers 43 and 44 to approximate a Bessel function.

When the mode switch is set to "GAUSSIAN" the inverters 41 and low level buffer amplifiers 45 and 47 are bypassed. More specifically, the input signal from the synthesize 30 is applied directly to the high level buffer amplifiers 46 and 48 in each respective channel after passing through additional shading potentiometers 49 and 50. As a consequence, in the GAUSSIAN mode, the amplitude of the signals applied to respective segments of the active electrode 12 are separately controlled, but they all have the same polarity, or phase. As is well-known in the art, the shading potentiometers 49 and 50 can be adjusted to alter the effective width of the Gaussian beam.

Figure 6:
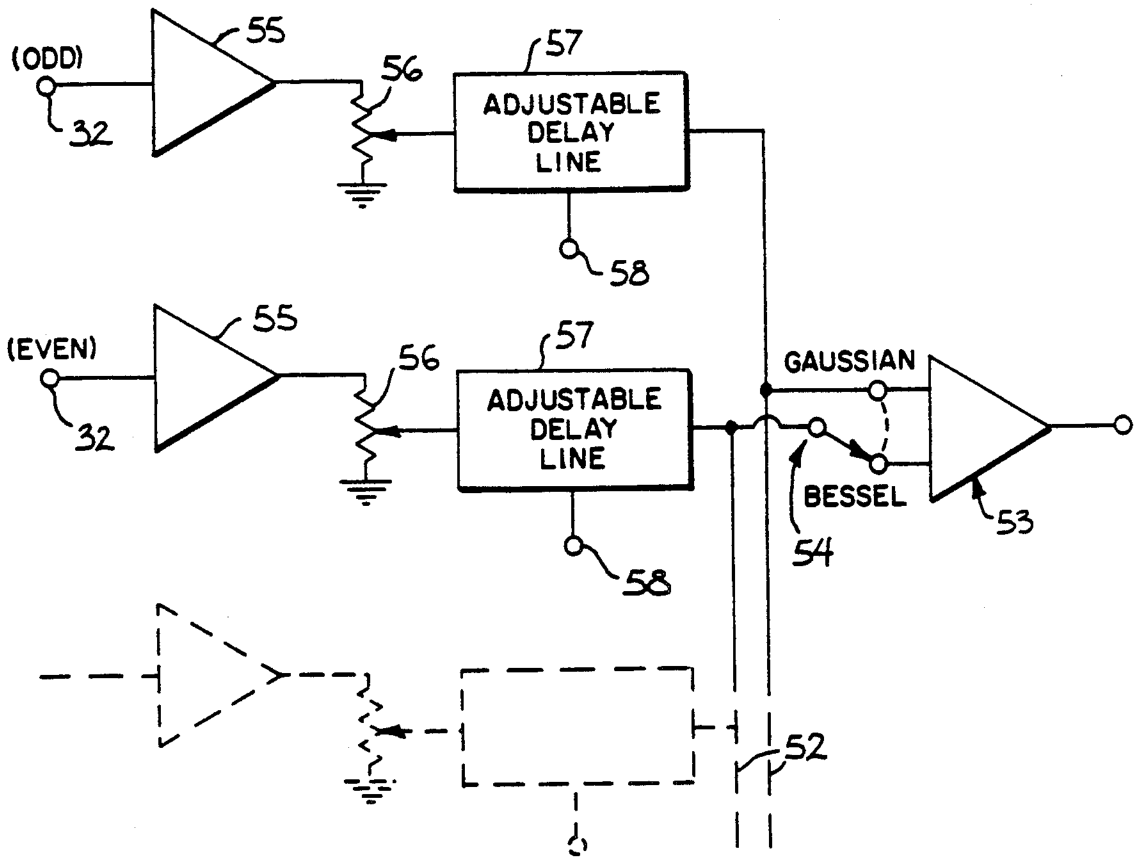
FIG. 6 is an electrical schematic diagram of a receiver which is employed in the system of FIG. 4.

Referring particularly to FIG. 6, the receiver 35 is comprised of ten separate channels which couple to the respective leads in the bus 32 to receive signals from the successive segments of the active electrode 12. Five of these channels connect to the odd numbered segments 13, 15, 17, 19 and 21 and five of these channels connect to the even numbered segments 14, 16, 18, 20 and 22. Only a single even and odd channel are shown in FIG. 6, and the additional channels are connected as shown by the dashed lines 52.

The ten channels in the receiver 35 are identical in construction, and their only difference is the manner in which they are connected to a summing amplifier 53. More specifically, the output of each odd numbered channel is connected to the non-inverting input of the summing amplifier 53, and the output of each even numbered channel is connected to a mode switch 54. The mode switch 54 is operable when set to a "GAUSSIAN" mode to also connect the even channels to the non-inverting input of amplifier 53, and it is operable when set to a "BESSEL" mode to connect the even channels to the inverting input of the amplifier 53.

Referring still to FIG. 6, each receiver channel includes a pre-amplifier 55 which amplifies the low level signal received from the ultrasonic transducer segment. The pre-amplifier drives a shading potentiometer 56, which may be set to adjust the level of the signal received from each segment of the active element 12. The adjusted signal is then input to an adjustable delay line 57 which has a control terminal 58 that is driven by the dynamic focusing control 36 (FIG. 4). As described in F. S. Foster, J. D. Larson, M. K. Mason, T. S. Shoup, G. Nelson, and H. Yoshida, "Development of a 12 element annular transducer for realtime ultrasound imaging," Ultrasound in Medicine and Biology, Vol. 15, No. 7, 1989, pp. 649–659, the dynamic focusing control circuit 36 operates the delay lines 57 to control the distance at which the system will focus the received signal when it is operated in the "GAUSSIAN" or "FRESNEL" mode. When in the "BESSEL" mode, the delay lines 57 are set to zero delay time.

The receiver 35 may thus be operated as a conventional Gaussian receiver in which the ten separate signals are adjusted in amplitude and time and then summed together. Or, in the alternative, the receiver 35 may be operated as a Bessel receiver in which the output is the difference between the sum of the odd numbered signals and the sum of the even numbered signals.

It should be apparent from the above described system, that it can be operated in a number of different modes. Both the transmitter 31 and the receiver 35 can be set to the GAUSSIAN mode in which the ultrasonic waves diffract, but are sharply focused at a selected distance from the transducer 10. On the other hand, both the transmitter 31 and the receiver 35 may be set to the BESSEL mode in which a non-diffracting beam of ultrasonic energy is emitted and received. For example, when operated in the GAUSSIAN mode, the preferred embodiment produces a main lobe which has a radius of 1.27 mm at a focal distance of 12 cm and a depth of field 2.4 cm. When operated in the BESSEL mode, the same transducer produces a nondiffracting beam that has a substantially constant radius of 1.27 mm throughout a depth of field of 20 cm. It is also possible to operate the transmitter 31 in the BESSEL mode to produce a nondiffracting beam, and to receive the echo signals in the GAUSSIAN mode with dynamic focusing to suppress the relatively high side lobes of the J Bessel beam. The following is a table which illustrates the various modes in which the preferred embodiment of the invention can be operated.

| Transmit Mode | Receive Mode | Reason |
|---|---|---|
| 1. Gaussian + one point focusing | Gaussian + dynamic focusing | Large depth of field in receive |
| 2. Bessel | Bessel | Nondiffracting deep depth of field transmit and receive |
| 3. Bessel | Gaussian + dynamic focusing | Suppress side lobes. Maintain deep depth of field in transmit |
| 4. Gaussian + one point focusing | Gaussian + same point focusing | High resolution and a given depth |

We claim:

1. An ultrasonic transducer system, the combination comprising:

a piezoelectric element having a pair of spaced, substantially flat surfaces;

an active electrode formed on one of the substantially flat surfaces of the piezoelectric element and having a st of separate segments which are disposed symmetrically about a central axis;

a ground electrode formed on the other of said substantially flat surfaces of the piezoelectric element; and a multi-channel transmitter for transmitting a signal having an ultrasonic frequency and producing an output signal at each of its channel outputs, which are applied across the ground electrode and respective ones of the active electrode segments, each channel having means for controlling the amplitude and phase of the signal output to its associated active electrode segment, such that a non-diffracting beam of ultrasound is launched form said one substantially flat surface of the piezoelectric element.

2. The ultrasonic transducer system as recited in claim 1 in which the central axis extends substantially perpendicular from said one flat surface of the piezoelectric element and the active electrode segments are formed as annular shaped rings disposed concentrically around the central axis.

3. The ultrasonic transducer system as recited in claim 1 in which the means for reversing the polarity of the output signal in alternate ones of the transmitter channels includes a signal inverter.

4. The ultrasonic transducer system as recited in claim 1 in which the multichannel transmitter includes switch means for changing the mode of operation of the system between a BESSEL mode in which the polarity of the output signals applied to successive ones of the respective active electrode segments is alternated, and a GAUSSIAN mode in which the polarity of the output signals applied to all of the active electrode segments is the same.

5. The ultrasonic transducer system as recited in claim 1 in which the dimensions of each active electrode segment and the amplitude of the signal applied to it are shaded such that the ultrasonic pressure distribution of the ultrasonic waves produced at the surface of the piezoelectric element approximates a zeroth-order Bessel function.

6. The ultrasonic transducer system as recited in claim 1 which further includes a multi-channel receiver for combining the input signals produced at the active electrode segments in response to ultrasonic waves impinging on the transducer to form an output signal, each channel of the multi-channel receiver having means for adjusting its gain, and each alternative ones of the receiver channels having means reversing the polarity of the input signal.

7. The ultrasonic transducer system as recited in claim 6 in which the multi-channel receiver includes switch means for changing the mode of operation of the system between a BESSEL mode in which the polarity of the input signals received from successive ones of the respective active electrode segments is alternated, and a GAUSSIAN mode in which the polarity of all the combined input signals is the same.

* * * * *

UNITED STATES PATENT AND TRADEMARK OFFICE

CERTIFICATE OF CORRECTION

Patent No. : 5,081,995

Dated : January 21, 1992

Inventor(s) : Jian-yu Lu, et al.

It is certified that error appears in the above-identified patent and that said Letters Patent is hereby corrected as shown below:

Col. line 3, insert the following:

This invention was made with U.S. Government support awarded by the National Institutes of Health (NIH) Grant No.: CA 43920. The U.S. Government has certain rights in this invention.

Signed and Sealed this

Nineteenth Day of August, 1997

Attest:

BRUCE LEHMAN

*Attesting Officer*

*Commissioner of Patents and Trademarks*